(12) United States Patent
Morishita et al.

(10) Patent No.: US 7,247,620 B2
(45) Date of Patent: Jul. 24, 2007

(54) METHOD OF TREATING SKIN WOUNDS WITH VECTORS ENCODING HEPATOCYTE GROWTH FACTOR

(75) Inventors: Ryuichi Morishita, Osaka (JP); Kuniaki Nakanishi, Saitama (JP); Yasufumi Kaneda, Osaka (JP); Hitoshi Kotani, Osaka (JP)

(73) Assignee: Anges MG, Inc., Toyonaka-shi, Osaka (JP)

( * ) Notice: Subject to any disclaimer, the term of this patent is extended or adjusted under 35 U.S.C. 154(b) by 164 days.

(21) Appl. No.: 10/477,166

(22) PCT Filed: May 9, 2002

(86) PCT No.: PCT/JP02/04529

§ 371 (c)(1),
(2), (4) Date: May 17, 2004

(87) PCT Pub. No.: WO02/089854

PCT Pub. Date: Nov. 14, 2002

(65) Prior Publication Data

US 2004/0234481 A1 Nov. 25, 2004

(30) Foreign Application Priority Data

May 9, 2001 (JP) .............................. 2001-139373

(51) Int. Cl.
*A01N 43/04* (2006.01)
*A01N 63/00* (2006.01)
*A01N 65/00* (2006.01)
*A61K 31/70* (2006.01)
*C07H 21/02* (2006.01)

(52) U.S. Cl. ....................... 514/44; 424/93.1; 536/23.5
(58) Field of Classification Search ..................... None
See application file for complete search history.

(56) References Cited

U.S. PATENT DOCUMENTS 5,827,703 A 10/1998 Debs et al.

FOREIGN PATENT DOCUMENTS

| EP | 0 847 757 A1 | 6/1998 |
| EP | 1210046 A | 12/2000 |
| EP | 1221490 A2 | 7/2002 |
| WO | WO 00/78259 A1 | 12/2000 |
| WO | WO 01/21761 A2 | 3/2001 |
| WO | WO 02/44393 A1 | 6/2002 |
| WO | WO 03/103721 A1 | 12/2003 |

OTHER PUBLICATIONS

Rinsch, et al. (2001) Gene Therapy, 8: 523-33.*
Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Cotsarelis, et al. (2001) Trends in Mol. Med., 7(7): 293-301.*
Otomo (2002) Nippon Yakurigaku Zasshi, 119(3): 167-74, Abstract Only.*
Jindo, et al. (1995) J. Dermatol. Sci., 10: 229-32.*
Meagher, et al. (2002) Austral. J. Dermatol., 43: 247-54.*
Boguniewcz, et al. (2006) J. Allergy Clin Immunol., 117(2): S475-80.*
Nayeri, et al. (2002) J. Dermatol. Treat., 13: 81-86.*
Game et al (2001) Wien Klin Wochenschr,113:823-38.*
Hamoen, et al. (2002) Cell Transplantation, 11: 385-95.*
Cioce, et al. (1996) J. Biol. Chem., 271(22): 13110-15.*
Ueda, et al. (1999) Ann. Thorac. Surg., 67: 1726-31.*
Rudinger (1976) Peptide Hormones, University Park Press, Baltimore, MD., pp. 1-7.*
Bowie, et al. (1990) Science, 247 : 1306-10.*
Sawamura, et al. (1997) J Invest Dermatol., 108: 195-99.*
Kunugiza et al., "Effective Acceleration of Wound Healing by Simultaneous Transfestion of Hepatocyte Growth Factor Gene and Prostacyclin Synthase Gene Using Shima Jet," *Mol. Ther.* 9:S397, #1036 (2004).
Nakanishi et al., "Gene Transfer of Human Hepatocyte Growth Factor into Rat Skin Wounds Mediated by Liposomes Coated with the Sendai Virus (Hemagglutinating Virus of Japan)," *Am. J. Pathol.* 161:1761-1772 (2002).
Corral et al., "Vascular Endothelial Growth Factor is More Important Than Basic Fibroblastic Growth Factor During Inchemic Wound Healing," *Arch. Surg.* 134:200-205 (1999).
Dunsmore et al., "Mechanisms of Hepatocyte Growth Factor Stimulation of Keratinocyte Metalloproteinase Production," *J. Biol. Chem.* 271:24576-24582 (1996).
Gille et al., "Transforming Growth Factor-α-Induced Transcriptional Activation of the Vascular Permeability Factor (VPF/VEGF) Gene Requires AP-2-Dependent DNA Binding and Transactivation," *EMBO J.* 16:750-759 (1997).
Hamoen et al., "Genetically Modified Keratinocytes in a Human Skin Model: Hepatocyte Growth Factor Promotes Wound Healing," *Surgical Forum* 50:582-584 (1999).
Kunisada et al., "Keratinocyte Expression of Transgenic Hepatocyte Growth Factor Affects Melanocyte Development, Leading to Dermal Melanocytosis," *Mech. Dev.* 94:67-78 (2000).

(Continued)

*Primary Examiner*—Joseph Woitach
*Assistant Examiner*—Robert M. Kelly
(74) *Attorney, Agent, or Firm*—Klarquist Sparkman, LLP

(57) ABSTRACT

The present invention relates to a therapeutic preventive agent that includes an angiogenic factor gene (such as hepatocyte growth factor (HGF), vascular endothelial growth factor (VEGF), fibroblast growth factor (FGF), and hypoxia inducible factor (HIF)) as its active ingredient, and the administration of such an agent into the targeted skin diseases-affected area.

7 Claims, 9 Drawing Sheets

OTHER PUBLICATIONS

Scheid et al., "Hypoxia-Regulated Gene Expression in Fetal Wound Regeneration and Adult Wound Repair," *Pediatr. Surg. Int.* 16:232-236 (2000).

Zeigler et al., "Growth Factor-Induced Epidermal Invasion of the Dermis in Human Skin Organ Culture: Expression and Role of Matrix Metalloproteinases," *Invasion Metastasis* 16:11-18 (1996).

Andree et al., "In vivo transfer and expression of a human epidermal growth factor gene accelerates wound repair," *Proc. Natl. Acad. Sci. USA* 91:12188-12192 (1994).

Eming et al., "Particle-Mediated Gene Transfer of PDGF Isoforms Promotes Wound Repair," *J. Invest. Dermatol.* 112:297-302 (1999).

Jeschke et al., "Biodistribution and Feasibility of Non-Viral IGF-I Gene Transfers in Thermally Injured Skin," *Lab. Invest.* 80(2):151-158 (2000).

\* cited by examiner

METHOD OF TREATING SKIN WOUNDS WITH VECTORS ENCODING HEPATOCYTE GROWTH FACTOR

PRIORITY CLAIM

This is a § 371 U.S. national stage of PCT/JP02/04529, filed May 9, 2002, and claims the benefit of Japanese Patent Application No. 2001-139373, filed May 9, 2001.

TECHNICAL FIELD

The present invention relates to the use of an angiogenic factor gene for skin disease. More specifically, the present invention relates to a therapeutic or preventive agent comprising an angiogenic factor gene as the active ingredient, and a method that comprises administering an angiogenic factor gene preventive to a target site. Examples of angiogenic factors include hepatocyte growth factor (HGF) vascular endothelial growth factor (VEGF), fibroblast growth factor (FGF), and hypoxia inducible factor (HIF) Examples of skin diseases include wounds, alopecia (baldness), skin ulcers, decubitus ulcers (bedsores), scars (keloids), atopic dermatitis, and skin damage following skin grafts such as autotransplantation and allotransplantation.

BACKGROUND ART

The expression "angiogenic factor" refers to a growth factor that not only stimulates neovascularization and angiogenesis (initiated along with the activation of parent blood vessel endothelial cells) in vivo, but is also mitogenic for endothelial cells in vitro. Examples of angiogenic factors include HGF, VEGF, FGF, and HIF. The first therapeutic application of angiogenic factors was reported by Folkman et al. (N. Engl. J. Med. 285, 1182-1186 (1971)). In later studies, the use of recombinant angiogenic factors such as the FGF family (Science 257, 1401-1403 (1992); Nature 362, 844-846 (1993)) and VEGF was confirmed as promoting and/or accelerating development of the collateral circulatory tract in animal models of myocardial and hind limb ischemia (Circulation 90, II-228-II-234 (1994)). Furthermore, the present inventors discovered that HGF, like VEGF, functions as an endothelium-specific growth factor (J. Hypertens. 14, 1067-1072 (1996)).

HGF is a cytokine discovered to be a powerful growth-promoting factor for mature stem cells, and its gene has been cloned (Biochem. Biophys. Res. Commun. 122: 1450(1984); Proc. Natl. Acad. Sci. USA. 83: 6489(1986); FEBS Letters 22: 231(1987); Nature 342: 440-443(1989); Proc. Natl. Acad. Sci. USA. 87: 3200(1991)). HGF is a plasminogen-related and mesenchymer-derived pleiotropic growth factor, and is known to regulate cell growth and cell motility in various types of cells (Nature 342: 440-443 (1989); Biochem. Biophys. Res. Commun. 239: 639-644 (1997); J. Biochem. Tokyo 119: 591-600(1996)). It is also an important factor in regulating blastogenesis and morphogenic processes during the regeneration of several organs. For example, HGF is a strong mitogen for epidermal cells such as hepatocytes and keratinocytes (Exp. Cell Res. 196: 114-120(1991)). HGF stimulates angiogenesis, induces cell dissociation, and initiates endothelial cell movement (Proc. Natl. Acad. Sci. USA. 90: 1937-1941(1993); Gene Therapy 7: 417-427(2000)) Later studies revealed that HGF not only functions in vivo as a hepatic regeneration factor in the repair and regeneration of the damaged liver, but also has an angiogenic effect and plays an important role in the therapy for or prevention of ischemic and arterial diseases (Symp. Soc. Exp. Biol., 47 cell behavior 227-234(1993); Proc. Natl. Acad. Sci. USA. 90: 1937-1941(1993); Circulation 97: 381-390(1998)). There are reports that administration of HGF to rabbit hind limb ischemia models showed remarkable angiogenesis, improved blood flow, suppression of decrease in blood pressure, and improvement of ischemic symptoms. As a result of these reports, HGF is now considered to be expressed as an angiogenic factor and to function as such.

As its name indicates, HGF was discovered in the liver. However, it actually exists throughout the entire body and has a cell-proliferating action. The vigorous cell division that occurs around an injury to repair the wound is also due to the action of HGF. The dermatology team at Juntendo University discovered that HGF is also a hair growth factor. HGF promotes hair growth by promoting division of hair matrix cells. Administration of HGF to hair matrix cells on scalps which show progressed androgen-related hair thinning is likely to regenerate thick hair.

Furthermore, HGF-induced angiogenesis in rat hearts with non-infarcted and infarcted myocardium (Proc. Natl. Acad. Sci. USA 90: 8474-8478(1993)), and in rat corneas (Proc. Natl. Acad. Sci. USA 90: 1937-1941(1993)) has been found in vivo.

Thus, HGF has a multitude of functions, not least of which is its function as an angiogenic factor. Various attempts have been made to utilize HGF in pharmaceutical agents, however, HGF's half-life in the blood has made this a problem. HGF's short half-life of about ten minutes makes maintenance of its blood concentration difficult. Thus, translocation of an effective HGF dose to an affected area is problematic.

VEGF is a dimeric glycoprotein that is mitogenic for endothelial cells and can enhance vascular permeability. VEGF's mitogenic effect is direct and specific to endothelial cells (Biochem. Biophys. Res. Commun., 161, 851-858 (1989)).

HIF promotes the production of erythrocytes and stimulates angiogenesis and erythropoietin (which increases oxygen supplied to the entire body). HIF is also the main transcription factor in the transcriptional activation of VEGF (which increases local oxygen supply), VEGF's receptor, and the genes for various enzymes involved in the glycolytic pathway (which provides resistance to cells by synthesizing ATP in anoxic conditions). HIF-1 is a heterodimer comprising HIF-1α and HIF-1β. HIF-1β (also called Arnt) also forms a heterodimer with the Ah receptor (which is associated with the metabolism of foreign substances such as dioxin) to function in the transcriptional regulation of drug-metabolizing enzyme genes.

In general, gene therapy can be used to treat various recovered clinical diseases (Science 256: 808-813(1992); Anal. Biochem. 162: 156-159(1987)). Selection of an appropriate vector for gene transfer is particularly important for successful gene therapy. Viruses, adenoviruses in particular, have been the preferred vectors for gene transfer. However, viral vectors are potentially dangerous when viral infection-associated toxicity, lowered immunity, and mutagenic or carcinogenic effects are considered. An example of an alternative method for gene transfer is the HVJ-liposome-mediated method, which has been reported to be effective in vivo. This method uses liposomes in combination with a viral envelope, and shows hardly any toxicity (Science 243: 375-378(1989); Anal. NY Acad. Sci. 772: 126-139(1995)). It has been successfully used for in vivo gene transfer into tissues including the liver, kidney, vascular wall, heart, and brain (Gene Therapy 7: 417-427(2000); Science 243: 375-378(1989); Biochem. Biophys. Res. Commun. 186: 129-134 (1992); Proc. Natl. Acad. Sci. USA. 90: 8474-8478(1993); Am. J. Physiol. 271(Regulatory Integrative Comp. Physiol. 40): R1212-R1220(1996)).

Wound healing comprises a succession of events including inflammation, angiogenesis, matrix synthesis, and collagen deposition, leading to re-endothelization, angiogenesis, and formation of granulation tissues (Clark R A F, "Overview and General Consideration of Wound Repair. The Molecular and Cellular Biology of Wound Repair." Plenum Press. New York (1996)3-50; Annu. Rev. Med. 46: 467-481(1995); J. Pathol. 178: 5-10(1996)). These healing processes are regulated by a number of mitogens and chemotactic factors, including growth factors such as fibroblast growth factor (FGF), transforming growth factor-α (TGF-α), transforming growth factor-β (TGF-β), epidermal growth factor (EGF), platelet-derived growth factor (PDGF), and vascular endothelial growth factor (VEGF) However, few studies have focused on the effect of HGF on wound healing (Gastroenterology 113: 1858-1872(1997)).

Although there are several reports on the transfer of genes such as IGF, PDGF, and EGF into wounds (Gene Therapy 6: 1015-1020(1999) Lab. Invest. 80: 151-158(2000); J. Invest. Dermatol. 112: 297-302(1999); Proc. Natl. Acad. Sci. USA 91: 12188-12192(1994)) none of these reports focus on the quantitative and qualitative changes in the number of factors involved in wound healing, or on histopathological effects after HGF gene transfer.

Re-epithilization of a wound occurs by translocation of keratinocytes from the edges of the wound toward its center. In vitro, HGF enhances proliferation, cell growth, and DNA synthesis in keratinocytes cultured under physiological $Ca^{2+}$ conditions (Exp. Cell Res. 196: 114-120 (1991)). Furthermore, due to enhanced cell turnover, HGF has been found to promote epithelial wound resealing in T84 intestinal monolayers (J. Clin. Invest. 93:2056-2065(1994)). In vivo administration of recombinant HGF has been found to promote regeneration of epithelial cells in rat kidneys damaged by anti-tumor agents (Gene Therapy 7: 417-427(2000)). However, in gastric ulcers produced in rats by cryoinjury, subcutaneous administration of recombinant HGF had no effect on the ulcer-healing rate, despite the increase of human HGF concentration in the serum. Epithelial cell proliferation increased in the borders of the ulcers eight to 15 days after cryoinjury (Gastroenterology 113: 1858-1872(1997)).

Transient upregulation of TGF-β expression is an important event in wound healing. TGF-β stimulates fibroblasts to produce matrix proteins, matrix protease inhibitors and integrin receptors, thereby modulating matrix formation and intercellular interactions at the wound site (Rokerts A B, Aporn M B: "Transforming growth factor-β. The Molecular and Cellular Biology of Wound Repair" Second Edition, by Clark R A F (Plenum Press. New York, 1996, 275-308)). Abnormal regulation and sustained overexpression of TGF-β1 would presumably contribute to an enhancement of tissue fibrosis, because increased expression of TGF-β1 mRNA has been reported in tissues of patients with cutaneous fibrosis (for example, hypertrophic scars and keloids) (Am. J. Pathol. 152: 485-493(1998)). Furthermore, TGF-β neutralizing antibodies not only reduced the cells in the wound granulation tissue of an adult wound, but also improved the architecture of the neodermis (Lancet 339: 213-214(1992)).

Proteinaceous formulations are generally administered intravenously. HGF has been administered in ischemic disease models both intravenously and intra-arterially (Circulation 97: 381-390(1998)). Such intravenous or intra-arterial administrations of HGF to animal models have revealed HGF's effectiveness on ischemic or arterial diseases. However, as yet, no conclusion has been reached with regard to a specific and effective method for administration, effective dose, and such. This is particularly so in the case of the HGF protein, due to the above-mentioned problems with half-life and transfer to the affected area. Thus, to date there has been no conclusion regarding an effective method of administration, effective dose, etc.

DISCLOSURE OF THE INVENTION

An objective of the present invention relates to a therapeutic or preventive agent for skin diseases that uses an angiogenic factor gene, and the use of these pharmaceutical agents.

The present inventors considered that HGF, which is an angiogenic factor, might promote epithelial repair and angiogenesis during wound healing. The present inventors investigated (i) whether, following gene transfer, human HGF mRNA and protein might distribute and deposit within full-thickness of wounds, (ii) whether the genetically transferred protein might be biologically active, and (iii) whether the transferred protein might have a biological effect on pathological conditions (for example, mitogen activity involving several cells within full-thickness of wounds, as well as re-epithelization in granulation tissues, angiogenesis, and deposition of the extracellular matrix, etc.).

Changes in wound tissues were also investigated to determine whether they related to TGF-β1 secretion. Measurements were made of the wound area, the concentration of human and rat HGF protein in wound tissue after HGF gene transfer, and the expression of the mRNA of other constitutive factors thought to be involved in wound healing such as TGF-β1, collagen type I (Colα2 (I)), collagen type III (Colα1 (III)) desmin, and vascular smooth muscle α-actin (α-sm-actin) A semiquantitative reverse transcription-polymerase chain reaction (RT-PCR) was used for these measurements. Morphogenic changes in the wound were investigated by in situ hybridization and immunohistochemical methods.

With these results, the present inventors demonstrated that direct administration of an angiogenic factor gene to a skin diseases-affected area is extremely effective. Specifically, it was found that in skin wounds, administration of an angiogenic factor gene yields effective results.

Because therapy with an angiogenic factor gene is non-invasive, the gene can be administered any number of times depending on the condition of the disease.

Specifically, the subject matter of this invention is as follows:

(1) a therapeutic or preventive agent for skin diseases comprising an angiogenic factor gene as the active ingredient;

(2) the therapeutic or preventive agent according to (1) wherein the angiogenic factor gene is an HGF gene, VEGF gene, FGF gene, or HIF gene;

(3) the therapeutic or preventive agent according to (1), wherein the skin diseases is a wound, alopecia (baldness), skin ulcer, decubitus ulcer (bedsore), scar (keloid), atopic dermatitis, or skin damage following a skin graft including autotransplantation and crosstransplantation;

(4) the therapeutic or preventive agent according to (1) or (2), wherein said therapeutic or preventive agent is in the form of a tablet, pill, sugar-coated agent, capsule, liquid preparation, gel, ointment, syrup, slurry, or suspension;

(5) the agent according to any one of (1) to (3), wherein said agent is used for transferring a gene into a cell by employing liposome entrapment, electrostatic liposomes, HVJ-liposomes, improved HVJ-liposomes, viral envelope vectors, receptor-mediated gene transfer, transfer of DNA into a cell using a particle gun (gene gun) direct introduction of naked-DNA, DNA transfer into a cell by ultrasonication, electroporation, or introduction using a positively charged polymer;

(6) a method for treating or preventing skin diseases, wherein the method comprises introduction of an angiogenic factor gene into a mammal; and (7) use of an angiogenic factor gene for producing a therapeutic or preventive agent for skin diseases.

The term "angiogenic factor gene" used in the present invention refers to a gene that can express an angiogenic growth factor. Herein, the term "angiogenic factor" refers to a growth factor that has not only been shown to stimulate in vivo neovascularization and angiogenesis (initiated along with activation of endothelial cells of the parent blood vessel), but has also been shown to be mitogenic for endothelial cells in vitro. Examples of the factor include HGF, VEGF, FGF, and HIF described hereinafter.

In the present invention, the term "HGF gene," as employed herein, refers to a gene that can express HGF (HGF protein). Specifically, the gene includes HGF cDNA (such as that described in Nature, 342, 440 (1989), Japanese Patent Publication No. 2577091, Biochem. Biophys. Res. Commun., 163, 967 (1989), Biochem. Biophys. Res. Commun., 172: 321 (1990)) where incorporated into appropriate expression vectors (e.g. non-viral vectors, viral vectors), such as those mentioned below. The nucleotide sequence of the cDNA encoding HGF is described in the aforementioned literature. The sequence is also registered in databases such as Genbank. Thus, by using DNA segments appropriate to the DNA sequence as PCR primers, HGF cDNA can be cloned in an RT-PCR reaction, using, for example, mRNA derived from liver or leukocytes. This cloning can be readily performed by one skilled in the art by referring to texts such as Molecular Cloning Second Edition, Cold Spring Harbor Laboratory Press (1989).

The term "VEGF gene," as employed herein refers to a gene that can express VEGF (VEGF protein). Specifically, such a gene is exemplified by VEGF cDNA incorporated into appropriate expression vectors (e.g. non-viral vectors, viral vectors) such as those mentioned below. Due to selective splicing during transcription, there are four subtypes of the VEGF gene in humans (VEGF121, VEGF165, VEGF189, and VEGF206) (Science, 219, 983 (1983); J. Clin. Invest., 84, 1470 (1989); Biochem. Biophys. Res. Commun., 161, 851 (1989)). Any of these VEGF genes can be used in the present invention. However, the VEGF165 gene is preferred as its biological activity is the strongest of the VEGF genes. The VEGF gene can also be readily cloned by one skilled in the art, based on the sequences described in the literature (Science, 246, 1306 (1989)) and the sequence information registered in databases. Modification of the VEGF gene can also be easily carried out.

The terms "FGF gene" and "HIF gene" as employed herein refer to genes that can express FGF and HIF respectively. Such genes are exemplified by genes incorporated into appropriate expression vectors (e.g. non-viral vectors, viral vectors) such as those mentioned below. Such genes can also be readily cloned by one skilled in the art, based on the sequences described in known literature and sequence information registered in databases. Modifications of these genes can also be easily carried out.

The angiogenic factor gene of the present invention is not limited to those mentioned above. So long as the protein expressed by the gene is effective as an angiogenic factor, the gene can be used as the angiogenic factor gene of the present invention. More specifically, the angiogenic factor gene of the present invention encompasses: 1) DNA that hybridizes under stringent conditions to the aforementioned cDNA; 2) DNA encoding a protein with the amino acid sequence of the protein encoded by the aforementioned cDNA, wherein one or more (preferably several) amino acids are substituted, deleted, and/or added; and such, so long as the DNA encodes a protein which is effective as the angiogenic factor of this invention. The DNA described above in 1) and 2) can be readily obtained, for example, by employing site-directed mutagenesis, PCR (Current Protocols in Molecular Biology edit., Ausubel et al. (1987) Publish. John Wiley & Sons Section 6.1-6.4), conventional hybridization (Current Protocols in Molecular Biology edit., Ausubel et al. (1987) Publish. John Wiley & Sons Section 6.3-6.4), etc.

Specifically, those skilled in the art can isolate DNA that hybridizes with a DNA described above by using the above-mentioned angiogenic factor gene or part thereof as a probe, or by using as a primer an oligonucleotide which specifically hybridizes with the angiogenic factor. Typical stringent hybridization conditions for isolating DNA encoding a protein functionally equivalent to the angiogenic factor are those of "1×SSC, 37° C." or the like; more stringently, those of "0.5×SSC, 0.1% SDS, 42° C." or the like; much more stringently, those of "0.1×SSC, 0.1% SDS, 65° C." or the like. As the hybridization conditions become more stringent, DNA more homologous to the probe sequence can be isolated. However, the above combinations of SSC, SDS, and temperature are only examples, and those skilled in the art can achieve stringencies equivalent to the above by appropriately combining these or other conditions that determine hybridization stringency (probe concentration, probe length, time of reaction, etc.).

When compared to proteins of known angiogenic factor, proteins encoded by genes isolated using hybridization or PCR typically demonstrate high homology at the amino acid level. The term "high homology" means sequence homology of at least 50% or more, preferably 70% or more, more preferably 90% or more (for example, 95% or more). The identity of amino acid and nucleotide sequences can be determined using the BLAST algorithm of Karlin and Altschul (Proc. Natl. Acad. Sci. USA 90:5873-5877, 1993). Based on this algorithm, programs such as BLASTN and BLASTX have been developed (Altschul et al. J. Mol. Biol. 215: 403-410, 1990). When nucleotide sequences are analyzed by BLAST-based BLASTN, the parameters are set, for example, as follows: score=100; and wordlength=12. Alternatively, when amino acid sequences are analyzed by BLAST-based BLASTX, the parameters are set, for example, as follows: score50; and wordlength=3. When BLAST and the Gapped BLAST program are used for the analysis, default parameters are used in each program. The specific techniques used in these analysis methods are already known (see, for example, the National Center for Biotechnology Information web site).

The following describes methods, forms, and amounts of gene transfer when gene therapy is employed as per the present invention.

When a gene therapy agent with the HGF gene as its active ingredient is administered to a patient, the form of administration can be classified into two groups: that using a non-viral vector, and that using a viral vector. Methods for the preparation and administration of these vectors are described in detail in experiment manuals (Jikken Igaku (Experimental Medicine) Supplementary Volume, "Idenshichiryo no Kisogijyutsu (Fundamental Techniques for Gene Therapy)", Yodosha, 1996; Jikken Igaku (Experimental Medicine) Supplementary Volume, "Idenshidonyu & Hatsugenkaiseki Jikkenho (Experimental Methods for Gene Transfer & Expression Analysis)", Yodosha, 1997; "Idenshichiryo Kaihatsu Kenkyu Handbook (Handbook of Gene Therapy Research and Development)", Nihon Idenshichiryo Gakkai (The Japan Society of Gene Therapy) Edition, NTS, 1999). Detailed explanations are given below.

A. Use of Non-Viral Vectors

A recombinant vector (where the target gene has been inserted into a conventional gene expression vector) can be used to insert a target gene into cells and tissues as per the methods below.

Examples of methods for gene transfer into cells include: lipofection, calcium phosphate co-precipitation, the use of DEAE-dextran, direct infusion of DNA using a glass capillary tube, electroporation, etc.

Methods for gene transfer into tissues include the use of: internal type liposomes, electrostatic type liposomes, HVJ (hemagglutinating virus of Japan)-liposomes, improved type HVJ-liposomes (HVJ-AVE liposomes), viral envelope vectors, receptor-mediated transfer, gene guns (the use of a particle gun to import a carrier such as metal particles along with DNA)., direct introduction of naked-DNA, positively charged polymers, ultrasonic irradiation, etc.

The aforementioned HVJ-liposome is constructed by incorporating DNA into a liposome formed by a lipid bilayer, then fusing this liposome with an inactivated Sendai virus (hemagglutinating virus of Japan: HVJ). The use of HVJ-liposomes is characterized by extremely high cell membrane fusion compared to conventional liposome methods, and is the preferred form of introduction. Methods of preparing HVJ-liposomes have been described in detail (Experimental Medicine Supplementary Volume, "Idenshichiryo no Kisogijyutsu (Fundamental Techniques of Gene Therapy)", Yodosha, 1996; Experimental Medicine Supplementary Volume, "Idenshidonyu & Hatsugenkaiseki Jikkenho (Experimental Methods for Gene Transfer & Expression Analysis)", Yodosha (1997); J. Clin. Invest. 93: 1458-1464(1994); Am. J. Physiol. 271: R1212-1220(1996), etc.). Use of the HVJ-liposome in transfection also includes, for example, the methods described in Molecular Medicine 30: 1440-1448(1993); Experimental Medicine, 12: 1822-1826(1994); Protein, Nucleic Acid, and Enzyme, 42, 1806-1813(1997); and preferably includes the method described in Circulation 92(Suppl. II): 479-482(1995).

The Z strain (available from ATCC) is the preferred HVJ strain, however in essence, other HVJ strains (for example, ATCC VR-907, ATCC VR-105, etc.) may be used.

Herein, the term "viral envelope vector" refers to a vector that incorporates a foreign gene into a viral envelope. Viral envelope vectors are gene transfer vectors in which the viral genome has been inactivated. Since viral proteins are not produced, the vector is safe and its cytotoxicity and antigenicity are low. By incorporating a gene into such a viral envelope vector (e.g. one that uses an inactivated virus), a highly efficient gene transfer vector that is safe for use with cultured cells and biological tissues can be prepared. Viral envelope vectors can be prepared, for example, using the method described in WO 01/57204 (PCT/JP01/00782). Examples of viruses used to prepare gene transfer vectors include both wild-type viruses and recombinant viruses, and such examples include Retroviridae, Togaviridae, Coronaviridae, Flaviviridae, Paramyxoviridae, Orthomyxoviridae, Bunyaviridae, Rhabdoviridae, Poxyiridae, Herpesviridae, Baculoviridae, and Hepadnaviridae. A viral envelope vector using HVJ is particularly suitable. Furthermore, a gene transfer vector can be prepared using a recombinant Sendai virus, as described by Hasan, M. K. et al. (Journal of General Virology, 78, 2813-2820 (1997)) or Yonemitsu, Y. et al. (Nature Biotechnology 18, 970-973 (2000)).

Direct transfer of naked-DNA is the most convenient of the methods mentioned above, and is thus the preferred method of introduction.

With respect to the present invention, any expression vector can be used so long as it can express the desired gene in vivo, and includes, for example, pCAGGS (Gene, 108, 193-200 (1991)), pBK-CMV, pcDNA3.1, or pZeoSV (Invitrogen, Stratagene).

B. Use of Viral Vectors

Viral vectors such as recombinant adenoviruses and retroviruses are typically used. More specifically, a desired gene is introduced into a DNA or RNA virus, such as an avirulent retrovirus, adenovirus, adeno-associated virus, herpes virus, vaccinia virus, poxvirus, poliovirus, Sindbis virus, Sendai virus, SV40, or immunodeficiency virus (HIV). The recombinant virus is then infected into the cell, thus introducing the desired gene.

Of the viral vectors mentioned above, the infection efficiency of adenoviruses is known to be much higher than other viral vectors. Thus, the use of the adenovirus vector system is preferred.

Methods for introducing an agent of the present invention during gene therapy include: (i) in vivo introduction of a gene therapy agent directly into the body; and (ii) ex vivo introduction of a gene therapy agent into a cell harvested from the body, followed by reintroduction of the modified cell into the body (Nikkei Science, April 1994, 20-45; Gekkann Yakuji 36 (1), 23-48, 1994; Jikken Igaku (Experimental Medicine) Supplementary Volume, 12 (15), 1994; "Idenshi-chiryo Kaihatsu Kenkyu Handbook (Handbook of Gene Therapy Research and Development)", Nihon Idenshichiryo Gakkai eds. (The Japan Society of Gene Therapy) Edition, NTS, 1999). The in vivo method is preferred in the present invention.

Various formulations (for example, liquid preparations) suitable for each of the above-mentioned methods of administration may be adopted as the form of the preparation. For example, an injection containing a gene as the active ingredient can be prepared by conventional methods which might include dissolving a gene in an appropriate solvent (e.g. a buffer solution, such as PBS, physiological saline, and sterilized water); sterilizing by filtration as necessary, and then loading into a sterile container. Conventional carriers and such like may be added to the injection as required. Alternatively, liposomes such as the HVJ-liposome can be prepared as suspensions, frozen agents, or centrifugally concentrated frozen agents.

For skin diseases, a therapeutic or preventive agent of this invention may be locally administered to the affected area of the skin, preferably in the form of an ointment. This ointment is an entirely homogenous semi-solid external agent with a firmness appropriate for easy application to the skin. Such an ointment normally includes fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture may be in the form of an oleaginous ointment, an emulsified ointment, or a water-soluble ointment oleaginous ointments use bases such as plant and animal oils and fats, wax, Vaseline and liquid paraffin. Emulsified ointments are comprised of an oleaginous substance and water, emulsified with an emulsifier. They may take either an oil-in-water form (O/W) or a water-in-oil-form (W/O). The oil-in-water form (O/W) may be a hydrophilic ointment. The water-in-oil form (W/O) initially lacks an aqueous phase and may include hydrophilic Vaseline and purified lanoline, or it may contain a water-absorption ointment (including an aqueous phase) and hydrated lanoline. A water-soluble ointment may contain a completely water-soluble Macrogol base as its main ingredient.

A pharmaceutically acceptable and preferable carrier is Vaseline containing 5% stearyl alcohol, or Vaseline alone, or Vaseline containing liquid paraffin. Such carriers enable pharmaceutical compositions to be prescribed in forms appropriate for patient consumption, such as tablets, pills, sugar-coated agents, capsules, liquid preparations, gels, ointments, syrups, slurries, and suspensions.

Alternatively, when locally administered into cells in an affected area or a tissue of interest, a therapeutic or preventive agent of this invention may contain a synthetic or natural hydrophilic polymer as the carrier. Examples of such polymers include hydroxypropyl cellulose and polyethylene glycol. A gene or vector of the present invention is mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used as the above-mentioned sheets.

Genes selected from angiogenic factor genes such as those used in the present invention (e.g. HGF, VEGF, FGF, HIF, etc.) may be used in multiple combinations or alone. Furthermore, factors other than the angiogenic factors mentioned above, and which are known to have an angiogenic effect, may also be used in combination or alone. For example, factors such as EGF have been reported to have an angiogenic effect, and such genes can be used. Furthermore, growth factors such as EGF have been reported to repair a variety of tissue cell injuries, and such genes may also be used.

Skin diseases according to the present invention includes wounds, alopecia (baldness), skin ulcers, decubitus ulcers (bedsores) scars (keloids), atopic dermatitis, and skin damage following skin grafts such as autotransplantation and crosstransplantation. Preventive agent, according to the present invention, refers to a pharmaceutical agent which prevents the onset (or incidence) of the above-mentioned diseases, or a pharmaceutical agent which reduces symptoms caused by the above-mentioned diseases, or a pharmaceutical agent which accelerates amelioration of these symptoms. These preventive agents are also included in the present invention.

Herein, "alopecia" refers to the phenomenon of thinning hair, where the hair cycle becomes extremely short, such that even thick hair falls out mid-growth, and as a result, the hairs that do grow are soft, fine and short. The expression "skin ulcers" means damage to deep tissues, reaching to the dermis or to the hypodermal tissue. Skin ulcers are categorized into ischemic ulcers, congestive ulcers, diabetic ulcers, decubitus ulcers, radiation ulcers instillation leakages, etc. "Decubitus ulcers" refers to a pathological condition where necrosis occurs by occlusion of a tissue's peripheral blood vessels due to continuous compression experienced at the contact surface of the body. Decubitus ulcers are intractable ulcers having a dry necrotic mass with a clear border, which form at sites of long-term compression, such as the back of the head, the back, and the hips of bedridden people. "Scars (keloids)" occur after skin damage and means hypertrophy of the connective tissue in which the wound surface produces a flat protrusion and sometimes forms claw-like projections. Some scars are proliferative, and continue to expand to the surrounding region, and beyond the original wound site. Factors that cause an external wound to form a keloid include systemic factors (such as genetic factors, age, and hormonal factors), and local factors (such as susceptibility to scars depending on the part of the body). Scars are categorized into hyperplastic scars, keloid scars, true keloids, etc.

Administration sites and methods for gene therapy agents of the present invention are selected such that they are appropriate to the disease and symptoms to be treated. The preferred administration method is parenteral administration. Furthermore, the preferred administration site is at the site of skin diseases. Herein, the term "site of skin diseases" refers to a site including the skin diseases-affected area and its surrounding region.

Specifically, administration to the skin diseases site can be carried out intravascularly, intramuscularly, and such, as well as by administration to surface layers with ointments and such Therefore, at the sites of wounds, baldness, decubitus ulcers (bedsores), keloids, atopic dermatitis, and skin grafts such as autotransplantation and crosstransplantation, angiogenesis in the affected area is enhanced, and blood flow is improved by intravascular and intramuscular administration using a syringe or catheter, or by surface application using an ointment or such. In this way, the function of the affected area can be recovered and normalized.

Application of an HGF gene of the present invention by active gene transfer allows treatment of wounds, baldness, skin ulcers, decubitus ulcers (bedsores), scars (keloids), atopic dermatitis, and skin damage following skin grafts such as autotransplantation and crosstransplantation, and enables functional recovery in patients for whom conventional therapeutic methods are not an appropriate option. A therapeutic or preventive agent of the present invention contains an angiogenic factor gene in an amount sufficient to accomplish the objectives intended by the pharmaceutical agent, i.e. it contains an angiogenesis gene in a "therapeutically effective amount" or a "pharmacologically effective amount". A "therapeutically effective amount" or "pharmacologically effective amount" is an amount of pharmaceutical agent required to produce the intended pharmacological results, and is the amount required to relieve the symptoms of the patient to be treated. Assays useful in confirming the effective dose for a particular application include methods for measuring the degree of recovery from target diseases. The amount that should actually be administered varies depending on the individual being treated, and is preferably an amount optimized to achieve the desired effects without marked side effects.

Therapeutically effective amounts, pharmacologically effective amounts, and toxicity can be determined by cell culture assays or optionally, by using appropriate animal models. Such animal models can be used to determine the desired concentration range and administration route for the pharmaceutical agent. Based on these animal models, one skilled in the art can determine the effective dose in a human. The dose ratio of therapeutic effect to toxic effect is called the therapeutic index, and this can be expressed as the ratio ED50:LD50. Pharmaceutical compositions with a large therapeutic index are preferred. An appropriate dose is selected according to the dosage form, the patient's sensitivity, age and other conditions, and the type and severity of the disease. Although the dose of a therapeutic agent of the present invention differs depending on the condition of the patient, the adult dose of an HGF gene is in the range of approximately 1 μg to approximately 50 mg, preferably in the range of approximately 10 μg to approximately 5 mg, and more preferably from the range of approximately 50 μg to approximately 5 mg.

A therapeutic agent of the present invention is preferably administered once every few days or few weeks, where the frequency of administration is selected such that it is appropriate to the patient's symptoms. A characteristic of the therapeutic agent of the present invention is that, due to its non-invasive administration, it can be administered any number of times depending on the symptoms.

With regards to the present invention, there are no restrictions regarding the animal into which the angiogenic factor gene can be transferred, however mammals are preferred. Examples of mammals include, without limitation, humans, and non-human mammals such as monkeys, mice, rats, pigs, cows and sheep.

BEST MODE FOR CARRYING OUT THE INVENTION

Figure 1:
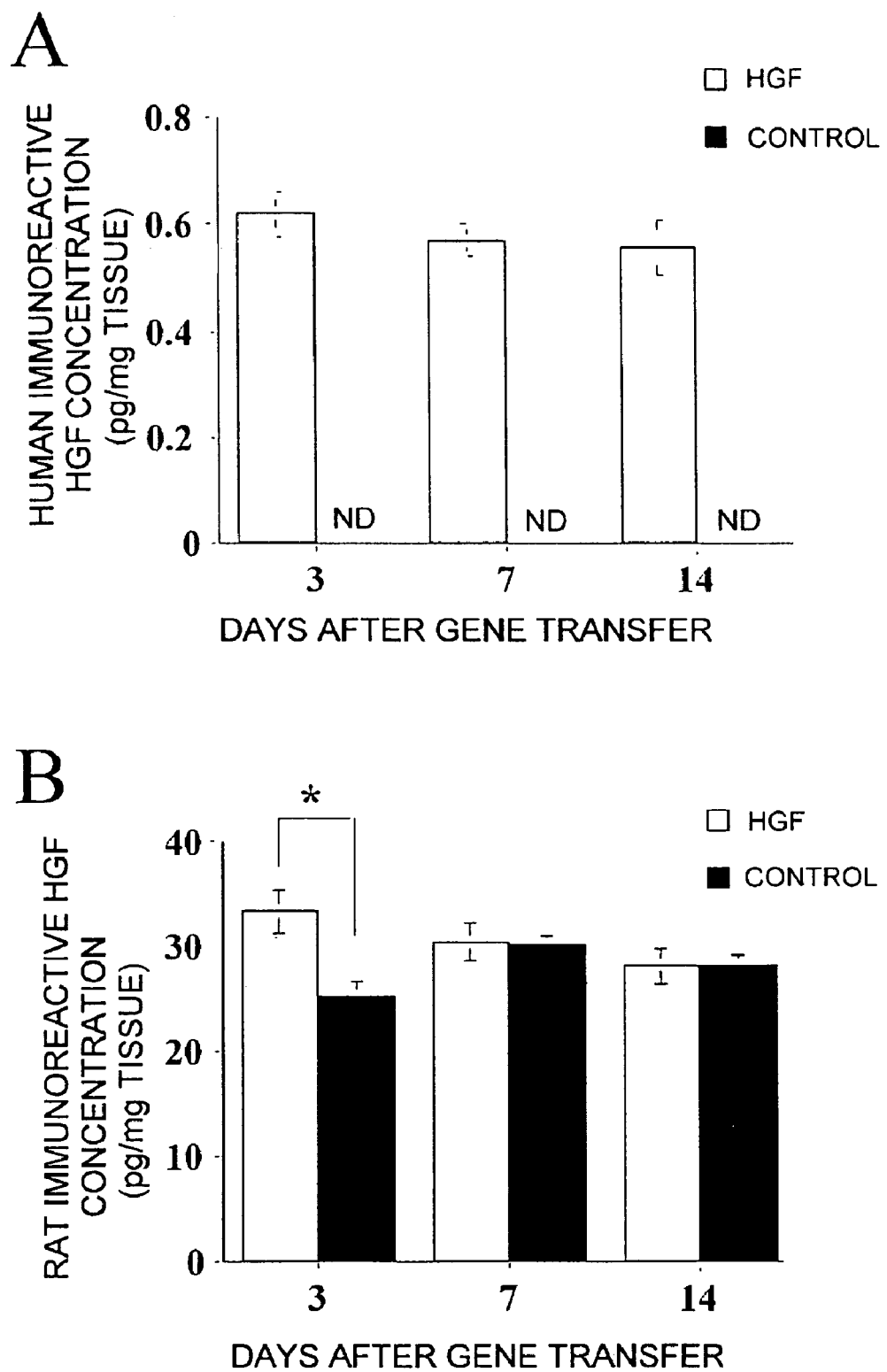
FIG. 1 shows human HGF concentration (A), and rat HGF concentration (B), in wounds after gene transfer. *, $p<0.05$ versus value for the control rats. n=5 for each group. ND: not detected.

Hereinafter, the present invention is specifically illustrated below with reference to Examples, but is not to be construed as being limited thereto.

(1) HGF Protein Concentration in Wound Tissues and in Plasma

1. Laboratory animals Sixty-five male Wistar rats, approximately eleven weeks old and weighing 310 g to 370 g, were assigned to one of two experiments, and then housed two per cage in a temperature-controlled room with a twelve-hour light-dark cycle. All rats were given commercial feed and tap water ad libitum. This experiment was performed in accordance with the Care and Use of Laboratory Animals of the National Institute of Health protocol. This protocol was approved by the Committee on the Ethics of Animal Experiments in the National Defense Medical College.

2. HGF expression vector Human HGF cDNA (2.2 kb) was inserted between the EcoRI/NotI sites of the pUC-SRα expression vector plasmid. In this plasmid, transcription of HGF cDNA is controlled by the SRα promoter (Nature 342: 440-443(1989)).

3. HVJ-liposomes (HMG)-1 (50 μl) purified from calf thymus was mixed with plasmid DNA (200 μg) in a total volume of 200 μl of isotonic solution (137 mM NaCl, 5.4 mM KCl, 10 mM Tris-HCl, pH 7.6) at 20° C. for one hour, and then this mixture was added to 10 mg of dry lipid (a 1:4.8:2 mixture of phosphatidylserine, phosphatidylcholine, and cholesterol). The liposome-DNA-HMG-1 complex suspension was mixed, ultrasonicated for three seconds, and then shaken for 30 minutes to form liposomes. Purified Sendai virus (HVJ) (Z-strain) was inactivated by UV irradiation (110 erg/mm$^2$/sec) for three minutes immediately before use. The liposome suspension (0.5 mL, containing 10 mg of lipid) was mixed with HVJ (30,000 hemagglutinating units) in a total volume of 3 mL of isotonic solution. After mixing, this was incubated at 4° C. for ten minutes, and then at 37° C. for 30 minutes with mild shaking. Free HVJ was removed by sucrose density gradient centrifugation. HVJ-liposome-DNA complex was collected from the top layer, and used immediately.

4. Wound tissues and blood samples Forty-one rats were divided into two groups (the HGF gene-transfer group and the control vector group) for biochemical and histological examination of wounds. The rats were anesthetized by intra-peritoneal injection of sodium pentobarbital (0.5 ml/kg), then the hair on their backs was shaved, the skin cleaned, and a 14 mm deep wound was made on the back of each animal. Three days later, these same rats (under pentobarbital anesthesia) received a subcutaneous injection of either HVJ-liposome (500 µl) containing 100 µg of HGF cDNA, or of a control vector. These injections were delivered to the edge of each wound using a 27-G needle. At 3, 7, and 14 days after the injection, the animals were decapitated under anesthesia, and blood samples were collected for HGF determination. The blood samples were placed in chilled tubes containing EDTA (2 mg/ml), and then centrifuged. The resultant plasma was frozen immediately, and stored at $-80°$ C. until analysis. At autopsy, the rats' skins were removed. The tissues of five rats per group were quantitatively determined and then cut in half. One half was frozen in liquid nitrogen and stored at $-80°$ C. until use.

5. ELISA test Tissue samples from five rats in each group were homogenized for one minute in four times their volume of 20 mM Tris-HCl buffer (pH 7.5) containing 0.1% 2 M NaCl, 0.1% Tween-80, 1 mM PMSF, and 1 mM EDTA, using a polytron homogenizer (24,000 rpm; Kinematica AG, Lucerne, Switzerland). The homogenate was centrifuged at 15,000×g for 30 minutes at 4° C. The supernatant and pellet were stored at $-80°$ C. until carrying out an enzyme-linked immunoabsorbent assay (ELISA) for HGF protein. Human HGF protein concentration was measured with ELISA, using an anti-human-HGF monoclonal antibody. Rat HGF concentration was also measured with ELISA, using an anti-rat-HGF monoclonal antibody (Institute of Immunology, Tokyo, Japan). The human HGF ELISA specifically detected human HGF, but not rat HGF. Plasma HGF protein concentration was measured in 50 L of rat plasma., using the above-mentioned ELISA.

6. Results ELISA revealed that human HGF protein levels were greatly increased at 3, 7, and 14 days after HGF gene transfer into the wound tissues of the HGF gene-transfer rats, and were not detected at all in the control rats (FIG. 1A). However, human HGF protein was not detected in plasma samples derived from the HGF gene-transfer rats. Rat HGF levels in the wound tissues of the HGF gene-transfer rats significantly increased for the first time three days after gene transfer (FIG. 1B, $p<0.05$).

(2) Expression of Human HGF mRNA and Protein in Wound Tissues

By a method similar to that described in (1), wounds were made on rats, and HVJ-liposome or control vector was administered, the animals were decapitated under anesthesia at 3, 7., and 14 days after injection, and the wound tissues thus obtained were fixed in periodate-lysine-paraformaldehyde (PLP) solution.

1. In situ hybridization In situ hybridization of HGF was carried out using deparaffinated 4% paraformaldehyde-fixed sections treated with 0.2 N HCl for 20 minutes, then incubated in 2×SSC for ten minutes at 37° C., and finally incubated in 5 µg/ml proteinase K for ten minutes at 37° C. Each section was then fixed in ~4% paraformaldehyde for five minutes, and incubated for ten minutes in 0.1 mol/L of triethanolamine buffer (pH 8.0) containing 0.25% (vol/vol) acetic anhydride to prevent non-specific binding due to tissue oxidation. The full-length human HGF cDNA (which was inserted between the EcoRI and NotI sites of the pUC-SRα expression vector plasmid) was digested by restriction enzymes for EcoRI. The resulting fragments of HGF cDNA (848 bp) were then ligated between the EcoRI cloning sites of pGEM-7Zf(+) (Promega, Madison, Wis.). The antisense probe and the corresponding sense probe were labeled with digoxigenin using SP6 and T7 polymerase respectively, by means of a RNA labeling kit (Boehringer Mannheim, Postfach, Germany). Hybridization was performed overnight at 42° C. in 50% (vol/vol) deionized formamide, 5× Denhardt's solution, 5% (weight/vol) dextran sulfate, 2×SSC, 0.3 mg/ml salmon-sperm DNA, 5 mM EDTA, and 0.01 µg/ml digoxigenin-labeled probes. After performing a final stringency wash at 55° C. for 20 minutes, hybridization was immunologically detected.

2. Immunohistochemistry The immunoperoxidase method was directly applied to the deparaffinated sections. A mouse monoclonal antibody against HGF was used (1:20; Institute of Immunology, Tokyo, Japan), and a horseradish peroxidase-labeled secondary antibody against rabbit immunoglobulin was used (Chemicon International Inc., 1:250 dilution). The mouse monoclonal antibody was specific to human HGF, and not rat HGF.

Figure 2:
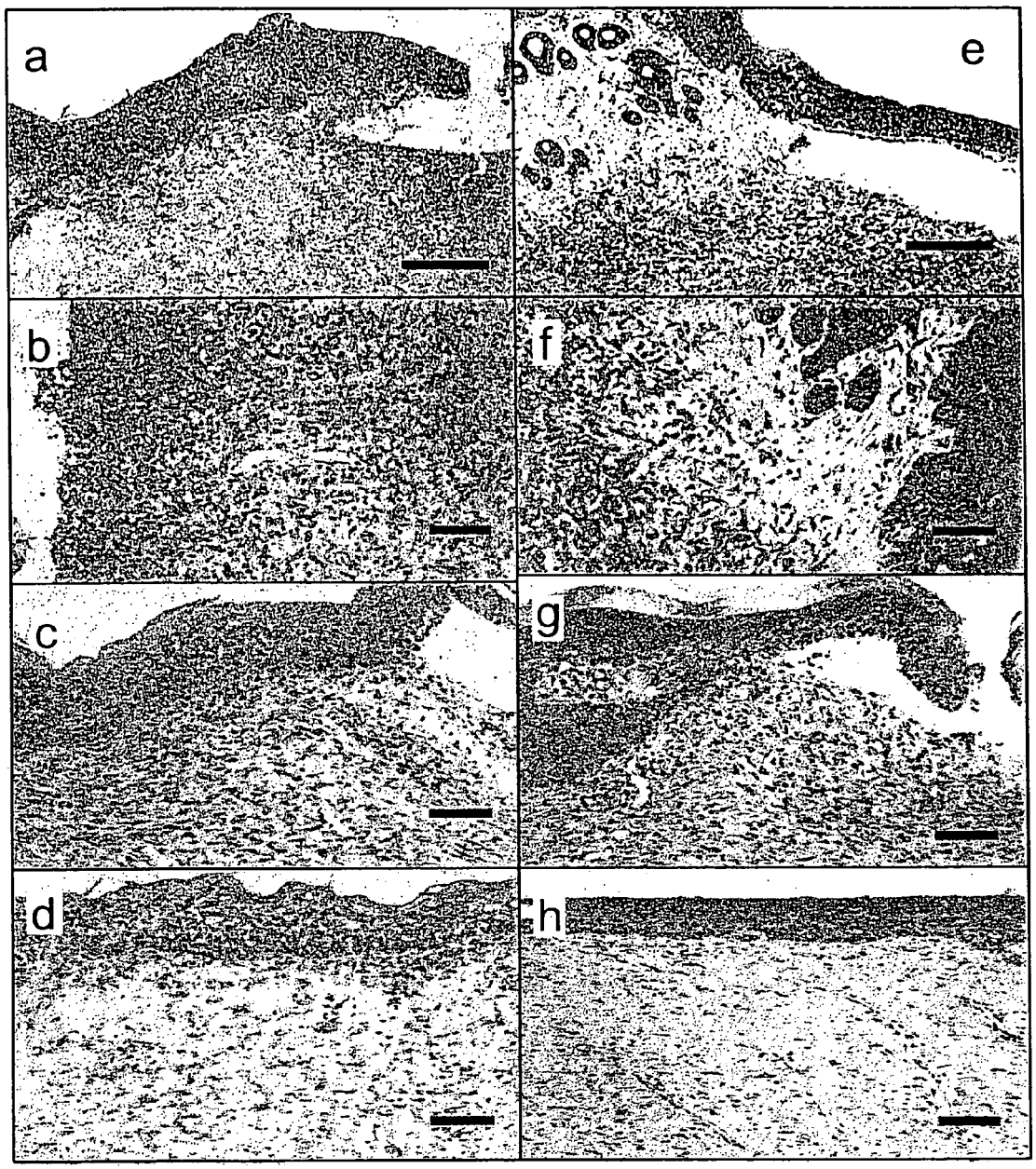
FIG. 2 is a set of photographs showing the distribution of human HGF mRNA (a to d) and protein (e to h) in HGF gene-transfer rats. Scale bars in the figure represent 100 μm in a and e, and 200 μm in b to d, f to h.

3. Results In the wound tissues of HGF gene-transfer rats, HGF mRNA was detected three days after gene transfer in squamous cells in the epithelium on the edge of the wound, in endothelial cells and smooth muscle cells of blood vessels, and in fibroblasts in the granulation tissues (FIG. 2a, 2b, 2e, and 2f). In contrast, HGF mRNA was not detected at all in the control rats. Similarly, human HGF protein was detected in the same cell types (squamous cells in the epithelium, endothelial cells and smooth muscle cells of blood vessels, and fibroblasts in the granulation tissues) of HGF gene-transfer rats, and was not detected in the control rats (FIGS. 2c and 2g). HGF expression was subsequently maintained up to 14 days after gene transfer (the last day of examination) (FIGS. 2d and 2h).

(3) Wound Lesion Size

By a method similar to that described in (1), wounds were made on rats, and HVJ-liposome or control vector was administered. Following gene (or vector) transfer, the wound areas of 20 rats were measured.

1. Measurement of wound area Wound area was measured from tracings taken at 0, 3, 7, 10, and 14 days after gene transfer, using an image analyzer (TOSPIX-U, AS3260C, and image analysis package software; Toshiba, Tokyo, Japan). Wound area was represented as a percentage of the initial area (as measured on day zero after gene transfer). The day of complete healing was taken to be the day that the epithelium completely closed the full extent of the full-thickness wound.

Figure 3:
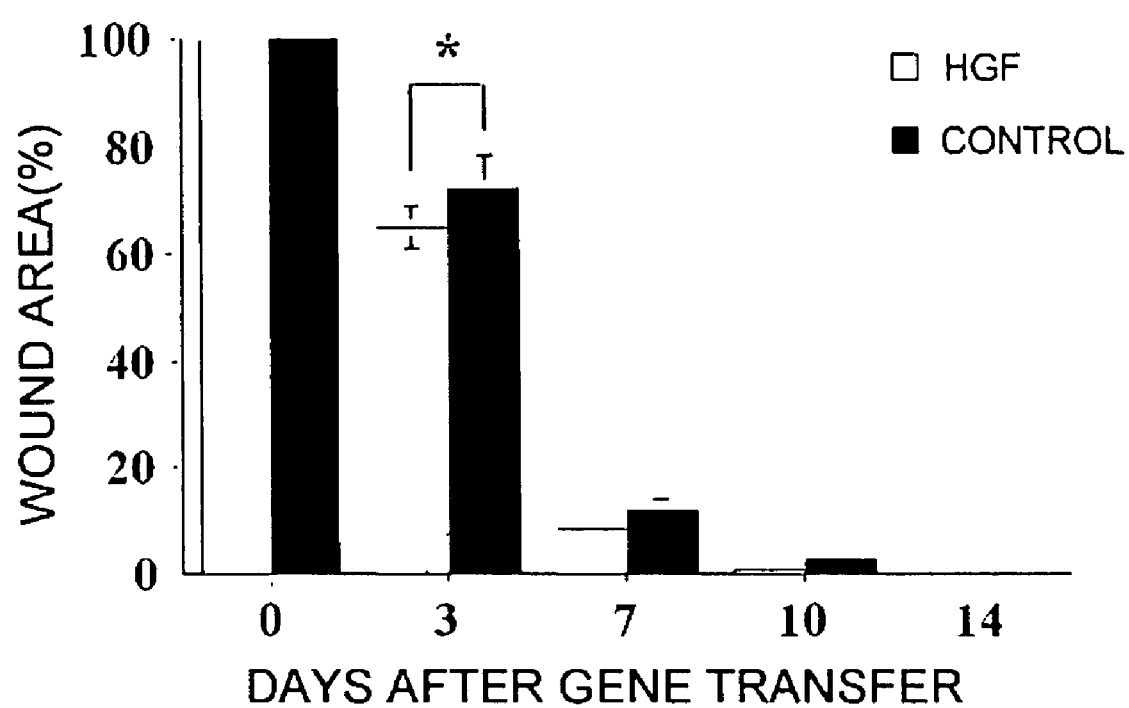
FIG. 3 shows the size of the wound area after gene transfer as a percentage of original wound area.

2. Results The wound lesion area (expressed as a percentage of the original wound lesion area on day zero after gene transfer) was significantly decreased in HGF gene-transfer rats (compared to control rats) from three days after gene transfer (FIG. 3, $p<0.05$). However, there was no difference between HGF gene transfer rats and control rats in the days required for complete healing.

(4) Cell Proliferation and Angiogenesis in Wounds

By a method similar to that described in (1), wounds were made on rats, HVJ-liposome or control vector was administered, the animal was decapitated under anesthesia at 3, 7, and 14 days after injection, and the wound tissues obtained were fixed in PLP.

1. Proliferating Cell Nuclear Antigen (PCNA) Measurements

Expression of PCNA in each tissue was detected as an index of cell proliferation. The immunoperoxidase method was applied directly to deparaffinated epithelium and granulation tissues. This method used mouse monoclonal antibody against PCNA (PC-10, 1:100, Dako Inc., Glostrup, Denmark), and horseradish peroxidase-labeled secondary antibody against rabbit immunoglobulin (Chemicon International Inc., dilution 1:250). Autoclave pretreatment in 0.01 M of citrate buffer solution (pH 6.0) was performed for 15 minutes at 120° C. before immunohistochemistry on PC-10. Incubation with a primary antibody was omitted as the negative control. For the PC-10 analysis, and on the basis of immunoreaction in at least 1,000 tumor cells, the percentage of nuclei with a positive immunoreaction was determined (PCNA index).

2. Measurement of angiogenesis Wound microvessel counts were evaluated by light microscopy in the areas containing the largest number of blood vessels. The number of blood vessels was determined in a continuous 200× field (20× objective lens and 10× ocular lens; 0.0925 mm² per field). Furthermore, in a similar manner to the method described in (1), angiogenesis was measured by investigating factor VIII in the epithelial cells of granulation tissues using a polyclonal antibody against factor VIII (1:100, Dako Inc., Glostrup, Denmark)

Figure 4:
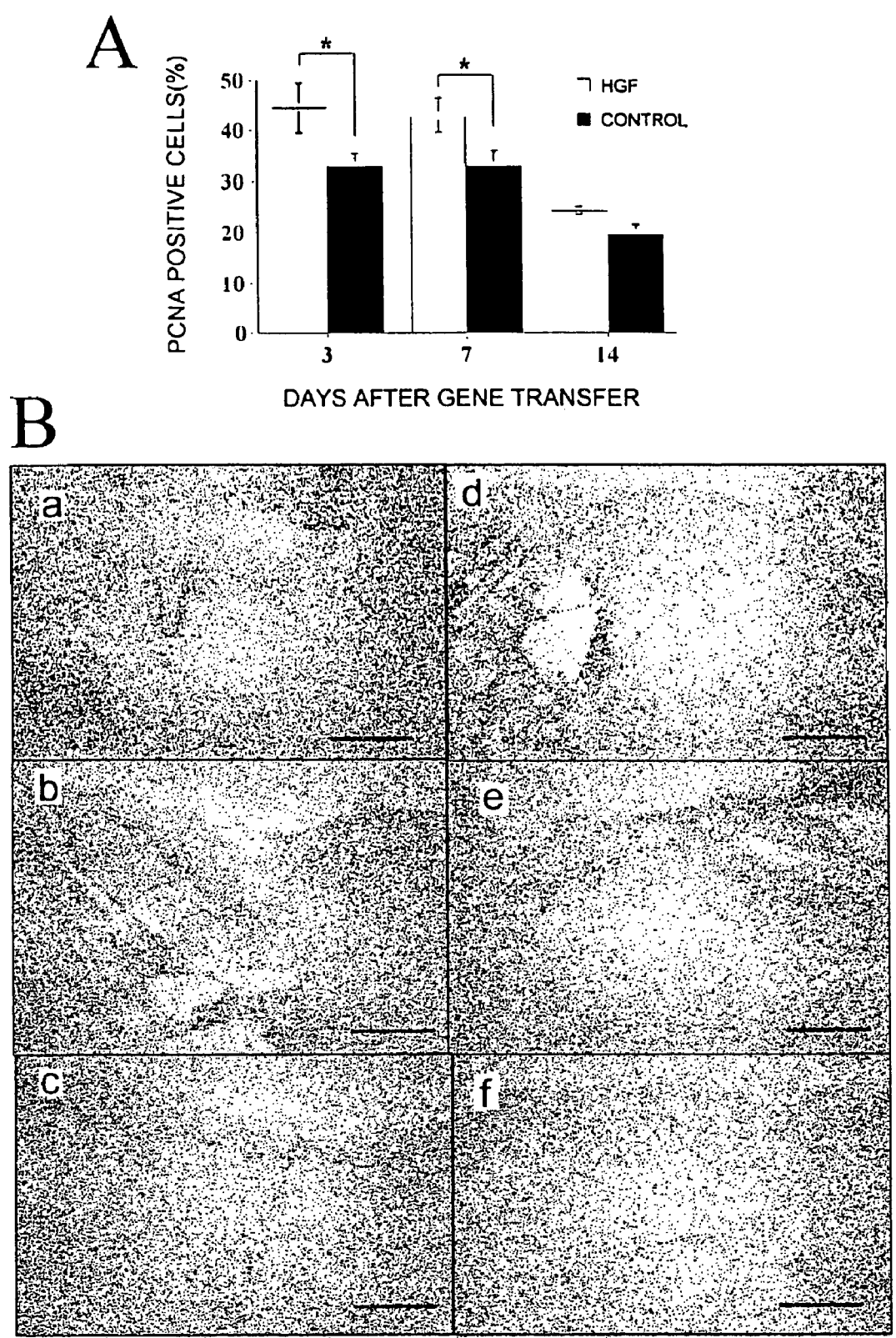
FIG. 4 is a graph (A), and a set of photographs (B), indicating expression of PCNA in the epidermis on the edge of the wound in rats after gene transfer. (A) shows the percentage of PCNA-positive cells in the epidermis after gene transfer, and (B) is a photograph showing the expression of PCNA. In the figure, a to c are photographs of HGF gene-transfer rats at days 3, 7, and 14 respectively, and d to f are photographs of control rats at days 3, 7, and 14 respectively. Scale bars represent 200 μm in a to f.
Figure 5:
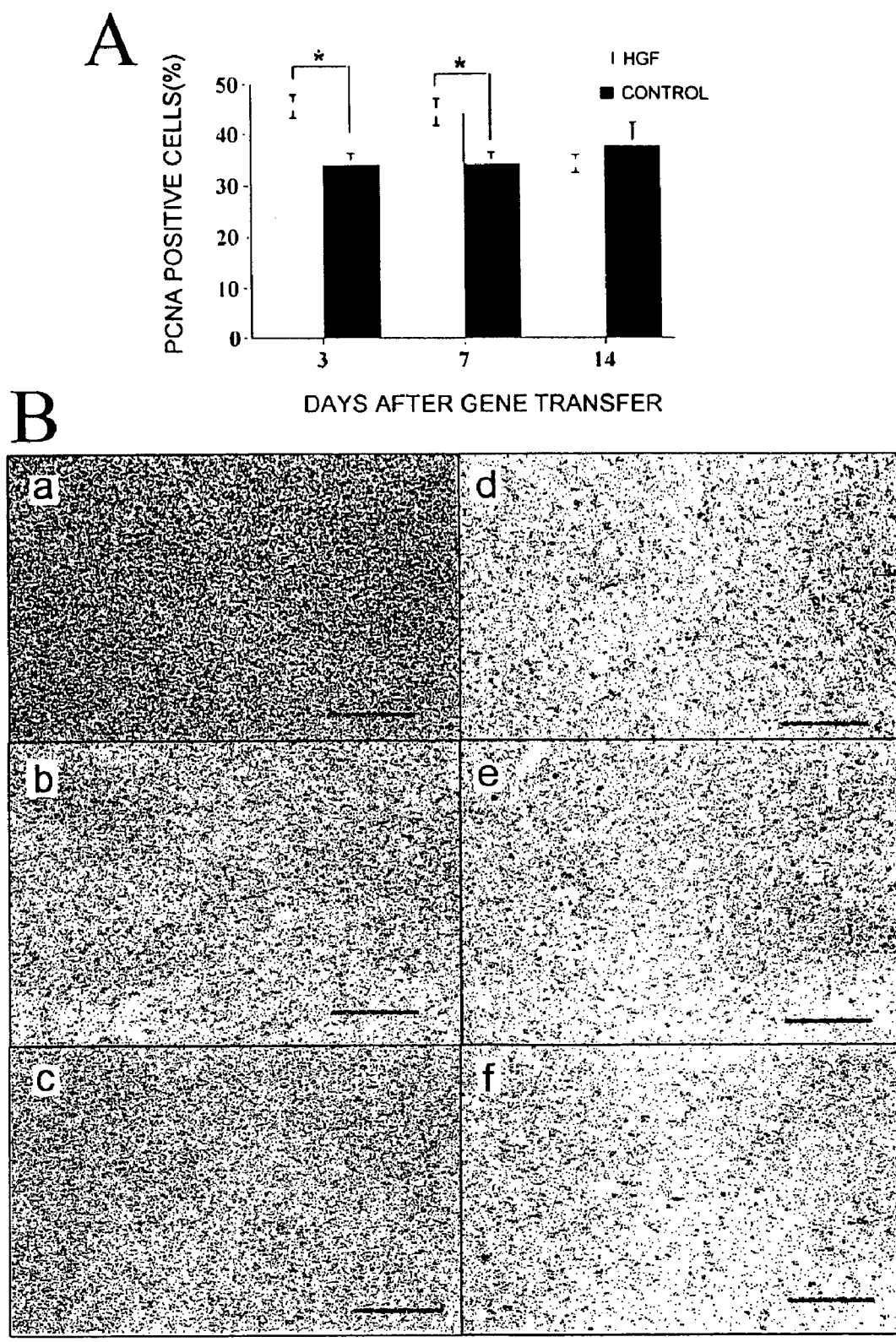
FIG. 5 is a graph (A), and a set of photographs (B), showing expression of PCNA in the granulation tissue of rats after gene transfer. (A) shows the percentage of PCNA-positive cells in the granulation tissue after gene transfer, and (B) shows the expression of PCNA. In the figure, a to c are photographs of HGF gene-transfer rats at days 3, 7, and 14 respectively, and d to f are photographs of control rats at days 3, 7, and 14 respectively. Scale bars represent 200 μm in a to f.
Figure 6:
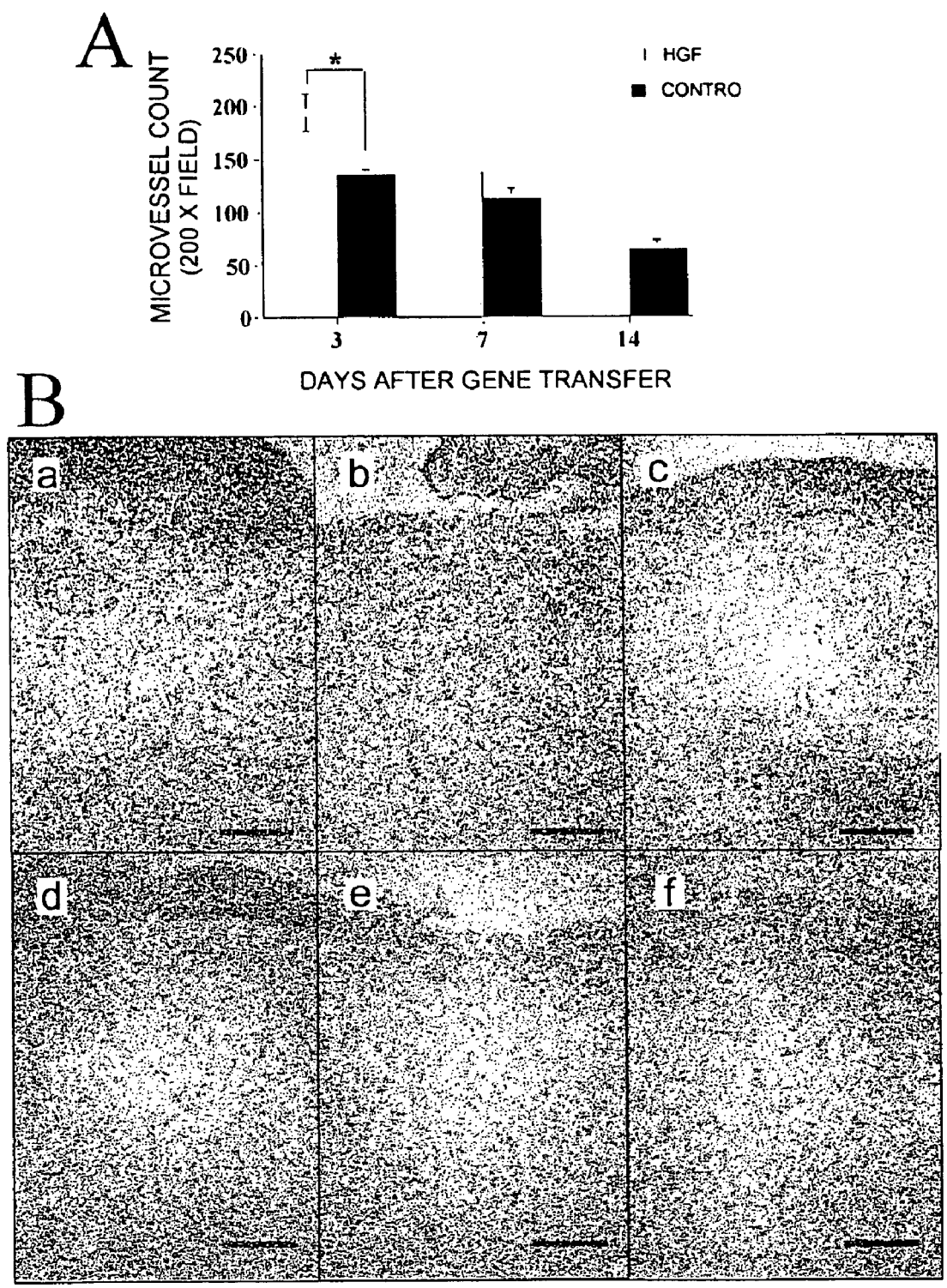
FIG. 6 is a graph (A), and a set of photographs (B), showing the microvessel count in the granulation tissue of rats after gene transfer by immunohistochemistry for factor VIII. (A) shows the microvessel count in the granulation tissue, and (B) shows the result of immunohistochemistry for factor VIII. In the figure, a to c are photographs of HGF gene-transfer rats at days 3, 7, and 14 respectively, and d to f are photographs of control rats at days 3, 7, and 14 respectively. Scale bars represent 200 μm in a to f.

3. Results PCNA indices in the epithelium on the edge of the wound and in granulation tissues were both significantly increased in HGF gene-transfer rats at three and seven days after gene transfer (compared to control rats) (FIGS. 4 and 5, $p<0.05$). Microvessel counts in the granulation tissues (as detected by immunohistochemistry for factor VIII) were significantly increased in HGF gene-transfer rats at three days after gene transfer (FIG. 6, $p<0.05$).

(5) Expression of Dermal Components in the Wound

By a method similar to that described in (1), wounds were made on rats, HVJ-liposome or control vector was administered, and RNA was extracted from the wound tissues of animals decapitated under anesthesia at 3, 7, and 14 days after injection.

1. Total RNA Extraction and Semi-Quantitative RT-PCR

Figure 7:
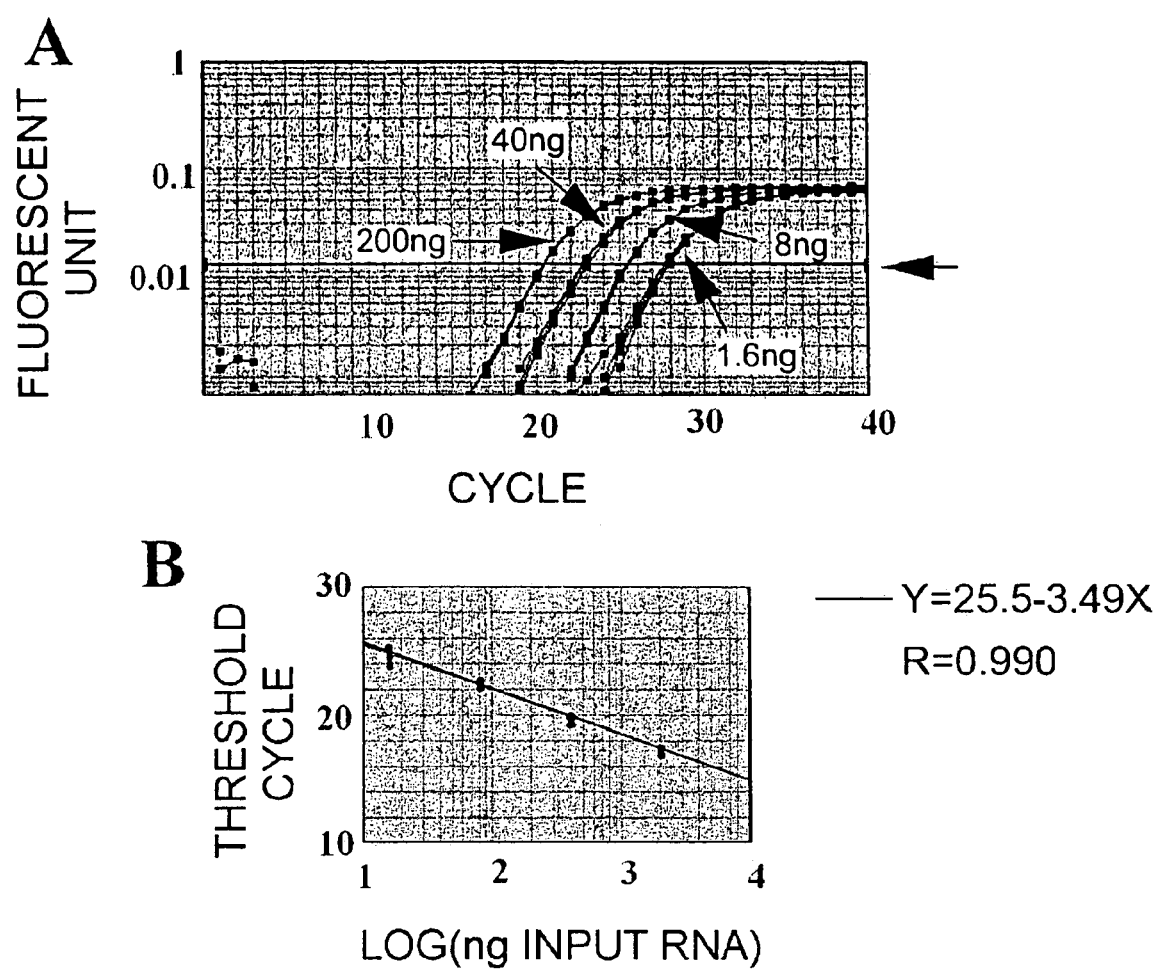
FIG. 7 shows the result of RT-PCR for Colα2 (I) mRNA. (A) is a real-time amplification plot for Colα2 (I), obtained using a semi-quantitative RT-PCR method. (B) is the standard curve for the threshold cycle of RT-PCR.
Figure 8:
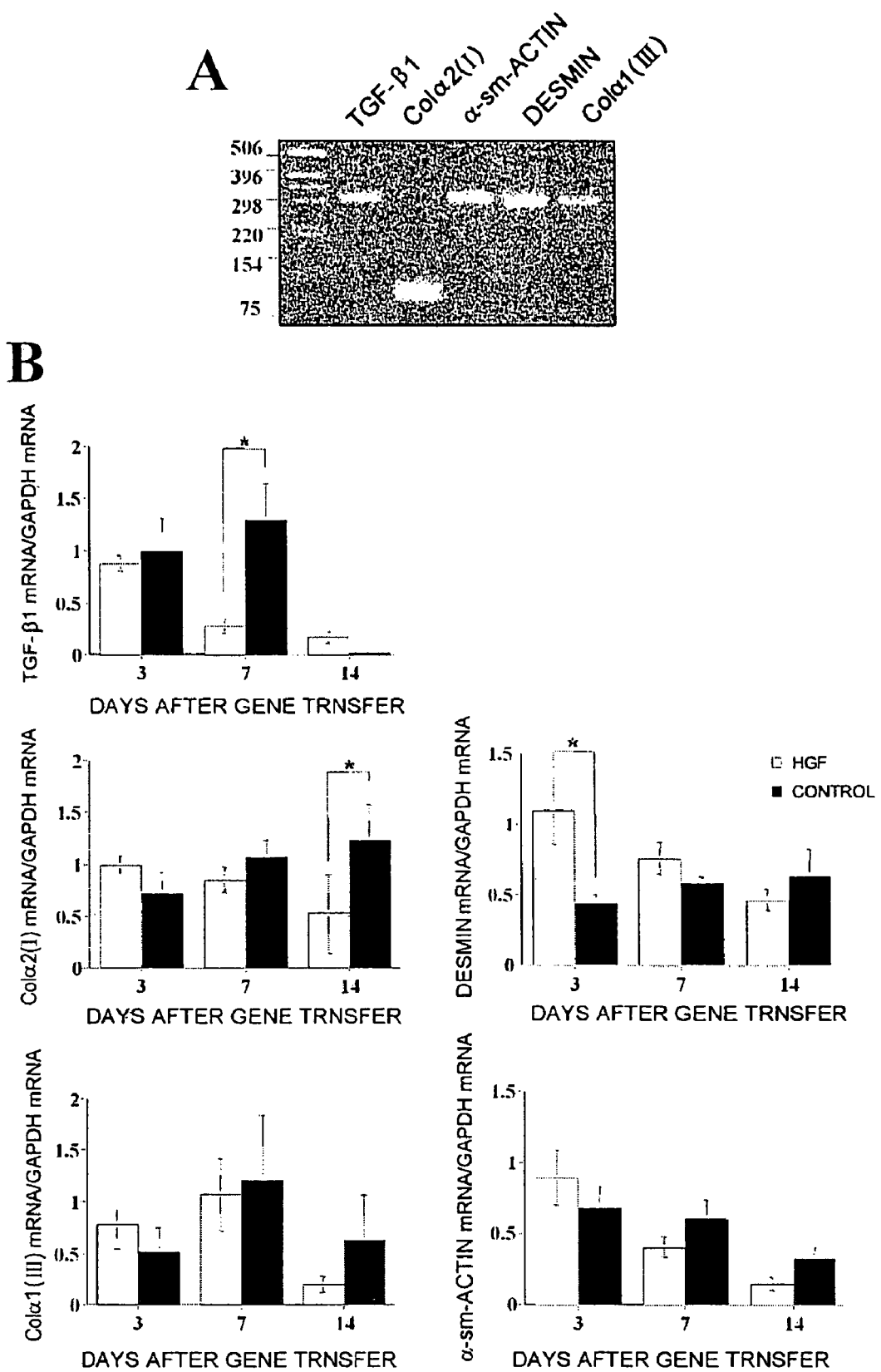
FIG. 8 is a set of graphs and a photograph indicating the results of RT-PCR for TGF-β1, Colα2 (I), α-actin, desmin, and Colα1 (III) mRNA. (A) shows the detection of PCR products, and (B) shows the results of semi-quantitative RT-PCR.

Semi-quantitative RT-PCR was used to examine the expression of various mRNA in the skin tissue of five rats in each group (Lab. Invest 79: 679-688(1999)). Total RNA in the skin tissues was isolated using acid guanidinium isothiocyanate-phenol-chloroform extraction and ethanol precipitation (Anal. Biochem. 162: 156-159(1987)). RT-PCR was performed using an amplification reagent kit (TaqMan EZRT-PCR kit; Applied Biosystems, Alameda, Calif.) with several primers. The following primers were prepared using an automated DNA synthesizer: TGF-β1, Colα2 (I), Colα1 (III), desmin, α-sm-actin, and glyceraldehyde-3-phosphate dehydrogenase (GAPDH). Table 1 shows the temperature conditions and sequence information for all of the PCR primers and TaqMan probes used (Hepatology 24: 636-642 (1996)). TaqMan probes were labeled at the 5'-end with a reporter dye molecule, FAM (6-carboxyfluorescein), and at the 3'-end with a quencher dye, TAMRA (6-carboxytetramethylrhodamine). The reaction master mix was prepared according to the manufacturer's protocol, giving final concentrations of 1× reaction buffer, 300 μM dATP, 300 μM dCTP, 300 μM dGTP, 600 μM dUTP, 3 mM Mg(OAc)$_2$, 0.1 U/μl rTth DNA polymerase, 0.01 U/μl AmpErase UNG, 900 nM primers, and 200 nM TaqMan probe. The RT reaction solution was incubated at 60° C. for 30 minutes, then at 95° C. for five minutes to inactivate AmpErase UNG. PCR was performed using an ABI PRISM 7700 Sequence detector (Applied Biosystems) During each PCR cycle, the TaqMan probe was cleaved by the 5'->3' exonuclease activity of rTth DNA polymerase, thereby increasing reporter dye fluorescence at the appropriate wavelength. The increase in fluorescence was proportional to the concentration of template in the PCR (FIG. 7A). Threshold fluorescence was set at 6.965 times the standard deviation of the average value obtained from the control without the template (following the protocol of the TaqMan RT-PCR kit). A standard curve was obtained using the threshold cycle established for each RNA level using four separate wells (FIG. 7B) PCR products were separated by electrophoresis in a 3% agarose gel, and stained with ethidium bromide (FIG. 8A).

TABLE 1

| mRNA | Sense primer (5'-3') | Antisense primer (5'-3') | TaqMan probe (5'-3') | Annealing temperature (C.) | Cycle | Size of product (bp) |
| --- | --- | --- | --- | --- | --- | --- |
| GAPDH | CTTCACCACC ATGGAGAAGG C SEQ ID NO:1 | GGCATGGACT GTGGTCATGA G SEQ ID NO:2 | CCTGGCCAAGG TCATCCATGAC AACTTT SEQ ID NO:3 | 60 | 40 | 238 |
| TGF-β1 | TGAGTGGCTG TCTTTTGACG TC SEQ ID NO:4 | GCAGTTCTTC TCTGTGGAGC TG SEQ ID NO:5 | CAGTGGCTGAA CCAAGGAGACG GAAT SEQ ID NO:6 | 64 | 50 | 301 |
| Colα2(I) | GGCTGCTCCA AAAAGACAAA TG SEQ ID NO:7 | CCAGAGGTGC AATGTCAAGG AA SEQ ID NO:8 | ATACAAAACGA ATAAGCCATCT CGCCTGCC SEQ ID NO:9 | 60 | 40 | 97 |
| Colα1(III) | GTGAAAGAGG ATCTGAGGGC TC SEQ ID NO:10 | GAGTTCAGGG TGGCAGAATT T SEQ ID NO:11 | TGCTGCCATTG CTGGAGTTGGA SEQ ID NO:12 | 64 | 50 | 302 |
| α-sm-actin | CGATAGAACA CGGCATCATC AC SEQ ID NO:13 | GCATAGCCCT CATAGATAGG CA SEQ ID NO:14 | AACTGGGACGA CATGGAAAAGA TCTGG SEQ ID NO:15 | 60 | 50 | 301 |
| Desmin | AGCGCAGAAT TGAGTCACTC | TGTCGGTATT CCATCATCTC | CTCAGGGACAT CCGTGCTCAGT | 60 | 50 | 301 |

TABLE 1-continued

| mRNA | Sense primer (5'-3') | Antisense primer (5'-3') | TaqMan probe (5'-3') | Annealing temperature (C.) | Cycle | Size of product (bp) |
|---|---|---|---|---|---|---|
| | AA SEQ ID NO:16 | CT SEQ ID NO:17 | ATGAGA SEQ ID NO:18 | | | |

GAPDH, rat glyceraldehyde-3-phosphate dehydrogenase;
TGF-β1, rat transforming growth factor-β1;
Colα2(I), rat α-2 type I collagen, segment 2;
Colα1(III), rat collagen type III α-1;
desmin, rat desmin;
α-sm-actin, rat vascular smooth muscle α-actin.

2. Results Expression of desmin mRNA in the wound tissues of HGF gene-transfer rats was significantly increased (compared to control rats) at three days after gene transfer, as determined by semi-quantitative RT-PCR. Expression of TGF-β1 and Colα2 (I) mRNA was significantly decreased at 7 and 14 days after gene transfer respectively (FIG. 8B, $p<0.0.5$).

(6) Hydroxyproline Concentration in the Wound

By a method similar to that described in (1)., wounds were made on rats, HVJ-liposome or control vector was administered, and tissue samples were prepared from wound tissues obtained from animals decapitated under anesthesia at 3, 7, and 14 days after injection.

1. ELISA test The samples were homogenized for one minute in four times their volume of 20 mM Tris-HCl buffer (pH 7.5) containing 0.1% 2 M NaCl, 0.1% Tween-80, 1 mM PMSF, and 1 mM EDTA, using a polytron homogenizer (24,000 rpm; Kinematica AG, Lucerne, Switzerland). The homogenate was centrifuged at 15,000×g for 30 minutes at 4° C., and the pellet was hydrolyzed in 6 N HCl at 110° C. for 16 hours. Hydroxyproline content was determined using an amino acid analyzer (Model 835; Hitachi Ltd. Tokyo, Japan).

Figure 9:
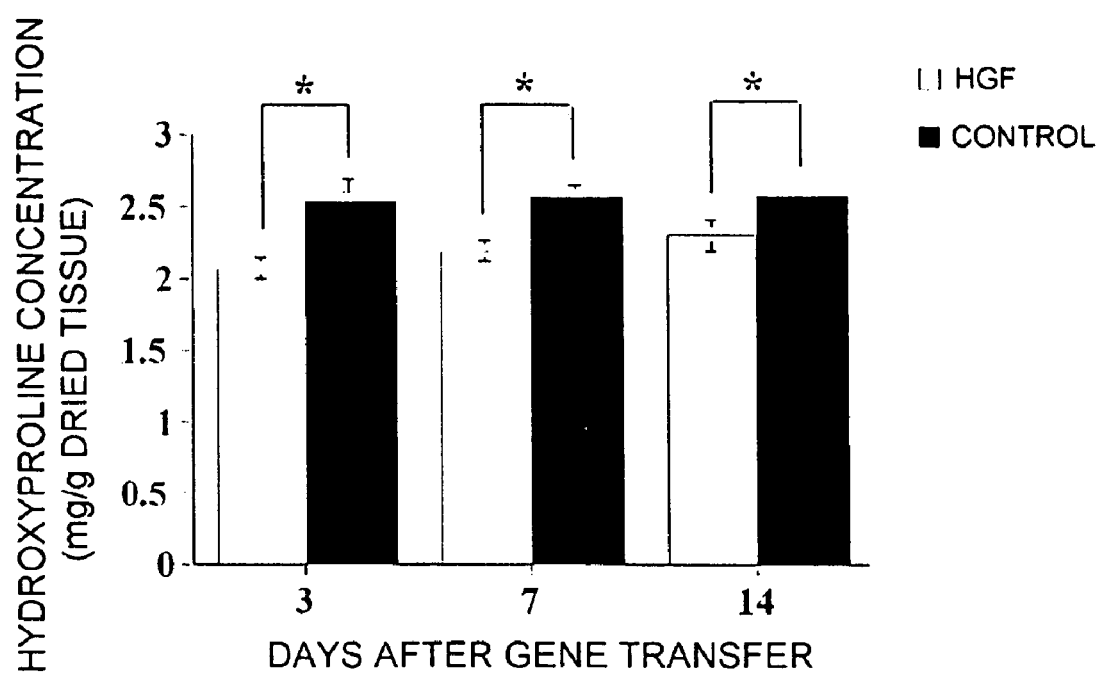
FIG. 9 shows the results of detecting hydroxyproline concentration in the wounds of rats after gene transfer.

2. Results At 3, 7, and 14 days after gene transfer, hydroxyproline concentration in the wounds of HGF-transfer rats was significantly lower than in the wounds of control rats (FIG. 9, $p<0.05$).

Each of the results obtained in the Examples above are expressed as a mean±standard deviation of the mean (SEM). When a significant F-value was obtained by analysis of variance (ANOVA), Fisher's protected least-significant-difference test was applied. $p<0.05$ was taken to be a significant difference.

INDUSTRIAL APPLICABILITY

Herein, an increased amount of human and rat HGF protein in the wound tissues of HGF gene-transfer rats, when compared to control rats, was observed using ELISA and immunohistochemistry. Similarly, using immunohistochemistry, the wound tissues of HGF gene-transfer rats were observed to experience rapid re-epithelization, intensive proliferation of several cell types, and intensive angiogensis. In contrast, during wound healing, down-regulation of TGF-β1 mRNA and Colα2 (I) mRNA, and a decrease in hydroxyproline levels in the wound were observed. According to these results, HGF gene transfer into a skin wound aids re-epithelization and angiogenesis, both elements of the wound healing process. HGF gene transfer may also suppress scar formation.

Sustained production of human HGF in the wound was confirmed at 14 days after gene transfer (the last day of the study) Furthermore, rat HGF concentration in the wounds of HGF gene-transfer rats was significantly higher than in the control rats at three days after gene transfer. Therefore, the human HGF gene may serve as a positive regulatory factor for the production of rat HGF. In addition, this result supports the hypothesis that HGF itself regulates local HGF production by auto-loop-positive feedback, where regulation occurs in an autocrine/paracrine manner [Kid. Int. 53: 50-58(1998); Biochem. Biophys. Res. Commun. 220: 539-545(1996)]. Thus administration of the HGF gene may promote primary HGF production in the individual receiving the administration.

The macroscopic and histological facts yielded by the present invention show that when compared with control rats, HGF gene-transfer rats exhibit hyperproliferation of basal cells in the epithelium at the edge of a wound, and a more rapid decrease in wound lesion area. Therefore, this model shows that increased HGF mRNA and protein expression enhances epithelial division and proliferation in the wound, and migration into and across the wound by paracrine and/or autocrine action. In the present invention, an increase in the number of blood vessels and PCNA-positive staining of endothelial cells in granulation tissues was observed in HGF gene-transfer rats, and these findings support HGF's strong angiogenic action.

In this invention, semi-quantitative RT-PCR was used to observe a decrease in TGF-β1 mRNA expression in HGF gene-transfer rats, when compared to control rats, at seven days after gene transfer. Furthermore, Colα2 (I) mRNA expression decreased at 14 days after gene transfer, and hydroxyproline decreased at 3, 7, and 14 days after gene transfer. These results suggest that scar formation in HGF gene-transfer rats may be suppressed by down-regulation of TGF-β1 synthesis. Accordingly, HGF gene transfer to the skin may be useful for treating patients with cutaneous fibrosis.

The above-mentioned results show that gene transfer of angiogenic factors is beneficial to the initial stages of wound healing, and that angiogenic factors may play a role in modulating skin diseases, and that manipulation of re-epithelization and angiogenesis by gene transfer-induced over-expression of angiogenic factors provides a novel therapeutic option in the field of wound healing.

The invention claimed is:

1. A method for accelerating the initial stage of skin wound healing, comprising direct administration of a plasmid or viral vector encoding a full length hepatocyte growth factor (HGF) to the wound, wherein the HGF is expressed, thereby accelerating the initial stage of skin wound healing.

2. The method of claim 1, wherein the plasmid or viral vector encoding a full length HGF is administered in the form of a liquid preparation, gel, ointment, syrup, slurry, or suspension.

3. The method of claim 2, wherein the plasmid encoding a full length HGF is administered in the form of HVJ-liposome.

4. The method of claim 2, wherein the plasmid encoding a full length HGF is administered in the form of viral envelope vector.

5. The method of claim 1, wherein the plasmid encoding a full length HUF is administered by liposome entrapment, electrostatic liposomes, HVJ-J-liposomes, improved HVJ-liposome, viral envelope vectors, receptor-mediated gene transfer, transfer of DNA into a cell using a particle gun (gene gun), direct introduction of naked-DNA, DNA transfer into a cell by ultrasonication, electroporation, or introduction using a positively charged polymer.

6. The method of claim 1, wherein the plasmid encoding a full length HGF is administered in the form of HVJ-liposome.

7. The method of claim 1, wherein the plasmid encoding a full length HGF is administered in the form of viral envelope vector.

* * * * *

UNITED STATES PATENT AND TRADEMARK OFFICE
CERTIFICATE OF CORRECTION

PATENT NO. : 7,247,620 B2  Page 1 of 1
APPLICATION NO. : 10/477166
DATED : July 24, 2007
INVENTOR(S) : Morishita et al.

It is certified that error appears in the above-identified patent and that said Letters Patent is hereby corrected as shown below:

Column 13, line 30, "50 L" should be --50 µL--.

Column 13, line 55, "~4%" should be --4%--.

Column 26, line 2, claim 5, "HUF" should be --HGF--.

Column 26, line 3, claim 5, "HVJ-J-liposomes" should be --HVJ-liposomes--.

Signed and Sealed this

Twenty-second Day of July, 2008

JON W. DUDAS
*Director of the United States Patent and Trademark Office*

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 1
cttcaccacc atggagaagg c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 2
ggcatggact gtggtcatga g                                              21

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:an
      artificially synthesized TaqMan probe sequence

<400> SEQUENCE: 3
cctggccaag gtcatccatg acaacttt                                       28

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 4
tgagtggctg tcttttgacg tc                                             22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 5
gcagttcttc tctgtggagc tg                                             22

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:an
      artificially synthesized TaqMan probe sequence

<400> SEQUENCE: 6

```
cagtggctga accaaggaga cggaat                                              26

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 7
ggctgctcca aaaagacaaa tg                                                  22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 8
ccagaggtgc aatgtcaagg aa                                                  22

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:an
      artificially synthesized TaqMan probe sequence

<400> SEQUENCE: 9
atacaaaacg aataagccat ctcgcctgcc                                          30

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
gtgaaagagg atctgagggc tc                                                  22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11
gagttcaggg tggcagaatt t                                                   21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized TaqMan probe sequence

<400> SEQUENCE: 12
```

```
tgctgccatt gctggagttg ga                                              22
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13

```
cgatagaaca cggcatcatc ac                                              22
```

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 14

```
gcatagccct catagatagg ca                                              22
```

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized TaqMan probe sequence

<400> SEQUENCE: 15

```
aactgggacg acatggaaaa gatctgg                                         27
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 16

```
agcgcagaat tgagtcactc aa                                              22
```

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 17

```
tgtcggtatt ccatcatctc ct                                              22
```

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:an
      artificially synthesized TaqMan probe sequence

```
<400> SEQUENCE: 18
ctcagggaca tccgtgctca gtatgaga                                          28
```